United States Patent [19]

Potts

[11] Patent Number: 5,305,765
[45] Date of Patent: Apr. 26, 1994

[54] CYSTOSCOPY SPLASH SHIELD

[75] Inventor: William E. Potts, Tallahassee, Fla.

[73] Assignee: Little Rapids Corporation, Green Bay, Wis.

[21] Appl. No.: 967,936

[22] Filed: Oct. 28, 1992

Related U.S. Application Data

[63] Continuation of Ser. No. 760,176, Sep. 16, 1991.

[51] Int. Cl.⁵ .............................................. A61F 13/00
[52] U.S. Cl. .................................. 128/849; 128/852; 128/853
[58] Field of Search ................ 128/849, 850, 851, 852, 128/853, 854, 855, 856

[56] References Cited

U.S. PATENT DOCUMENTS

| | | | |
|---|---|---|---|
| 2,715,902 | 8/1955 | Shaffer et al. | 128/853 |
| 3,410,266 | 11/1968 | Krzewinski et al. | 128/849 |
| 3,766,913 | 10/1973 | Balin | 128/853 |
| 3,797,484 | 3/1974 | Ericson | 128/853 |
| 3,862,632 | 1/1975 | Hinsch | 128/849 |
| 3,930,497 | 1/1976 | Krebs et al. | 128/853 |
| 3,942,523 | 3/1976 | Rudtke | 128/853 |
| 4,275,719 | 6/1981 | Mayer | 128/849 X |
| 4,690,137 | 9/1987 | Starzmann | 128/849 |
| 4,807,644 | 2/1989 | Sandhaus | 128/849 |
| 4,903,710 | 2/1990 | Jessamine et al. | 128/849 |
| 4,905,710 | 3/1990 | Jones | 128/849 |

Primary Examiner—Robert A. Hafer
Assistant Examiner—Sam Rimell
Attorney, Agent, or Firm—Niro, Scavone, Haller & Niro

[57] ABSTRACT

A cystoscopy splash shield for use during surgery in which a large volume of human liquid is involved. The splash shield includes a rectangular shaped transparent plastic sheet with a strip of adhesive along its short edge and a hole present in the approximate middle of the sheet. The short edge of the plastic sheet is affixed to the torso of the patient by the adhesive strip. The remaining portion of the shield is draped over the groin area of the patient with overlap over and between the patient's legs. The shield is positioned so its hole is over the groin area to undergo surgery. A medical optical instrument may be inserted into the hole which is sealed around its circumference. As a result, a physician conducting surgery in the groin area is protected from any splashing fluids from the patient.

2 Claims, 1 Drawing Sheet

CYSTOSCOPY SPLASH SHIELD

This is a continuation of copending application(s) Ser. No. 07/760176 filed on Sep. 16, 1991.

BACKGROUND OF THE INVENTION

This invention relates generally to a splash shield for use by surgeons during high-fluid surgical procedures and more particularly to a cystoscopy splash shield designed to accommodate an eyepiece of an endoscope or any other similar optical-medical device.

The prior art has concentrated on protecting sterile, prepared areas of the patient from contamination by non-sterile areas (see, for example, U.S. Pat. Nos. 4,414,968 (Amin); 4,462,396 (Wickman); 4,378,794 (Collins); 4,489,720 (Morris, et al.); 4,890,628 (Jackson); 4,974,604 (Morris)). But efforts to protect the physician from contaminated body fluids have been unsatisfactory. Such protection is desirable because the fluids may contain disease-causing agents such as the HIV virus.

In U.S. Pat. No. 4,834,068, for example, Gottesman discloses a disc-shaped, rigid plastic splash shield that attaches to the eyepiece of an endoscope or similar instrument, providing some protection for the physician's face. Splashing blood or irrigation fluid simply rebounds from the rear face of the splash shield and drips onto the floor, or runs down the surface of a conventional surgical drape, or off of the physician's clothing. U.S. Pat. No. 4,848,322 (Dash, et al.) discloses a similar rigid face shield, which is rectangular and curved slightly to wrap around the physician's face. Also, U.S. Pat. No. 4,535,481 (Ruth-Larson, et al.) discloses a protective gown with a broad skirt and fluid-impermeable areas that can be worn by the physician for protection during high-fluid procedures.

Aside from these prior art devices, the only protection afforded the physician by prior art devices consists of channelling blood and irrigation fluids, and sometimes feces, into disposal bags, or into a trough and drain arrangement sometimes provided on operating tables used for procedures such as cystoscopies (see U.S. Pat. No. 4,378,794 (Collins)). U.S. Pat. No. 4,903,710 (Jessamine, et al.) discloses such a device that channels or irrigates the bodily fluids away from the physician. Jessamine et al. describes a fluid protection drape arrangement suitable for attachment to the elevated legs and feet of a patient who has been placed in the lithotomy position on his or her back in the stirrups used for gynecological or proctological procedures.

A surgical drape providing a lesser degree of protection is disclosed in U.S. Pat. No. 4,471,769 (Lockhart). That patent discloses a multi-section drape suitable for use on patients in the lithotomy position. Lockhart's drape comprises a hammock-shaped member 8 attached at one end to the drape covering the patient at the position near the patient's buttocks, and at the other end to the physician's chest by means of elastic strips 40. One or more fenestrations (34, 36) are provided in the distal end of the hammock-shaped member, allowing access to the patient's genitals. Blood and irrigation fluid run out the holes and down the hammock-shaped member, to a drain 38 at its bottom. The physician's hands and face remain exposed to the blood and irrigation fluid running down the hammock-shaped member.

U.S. Pat. No. 4,926,882 (Lawrence) discloses a clear plastic bag intended to protect a physician conducting an autopsy from body fluids, blood, and bone fragments dispersed in the air by an oscillating bone saw. It would be unsuitable for use on live patients.

In short, the prior art intended for use with live patients teaches only the masks disclosed in Gottesman, which offer only limited protection to the physician's face; and the complex drapes described by Jessamine and Lockhart, which are usable only for procedures in which the patient is placed in the lithotomy position, and which allow only partially-protected access to the patient, and then only from a position directly behind the patient's buttocks. My invention is directed to overcoming the aforementioned limitations and problems in prior art devices.

SUMMARY OF THE INVENTION

My invention preserves the advantages of prior art splash shields and drapes while providing new advantages not found in currently available devices. Furthermore, my invention overcomes many of the disadvantages of such currently available splash shields and drapes.

My invention relates to an splash shield formed from an impermeable plastic sheet of rectangular shape, with an adhesive strip at one edge suitable for attachment directly to the patient's torso, or to a conventional drape of the sort used for any high-fluid surgical procedures, such as uro-genital or rectal surgery. The splash shield may be pierced by an aperture or a hole located at the apex of two lines of perforated tear slits oriented at right angles to each other. The hole is suitably sized to fit over the eyepiece of an endoscope or similar optical-medical device, or a nephroscope of the sort used for nephrolithotripsy procedures. Alternatively, a variety of adhesive, Velcro ®, elastic, or mechanical attachment means can be used at the location of the hole to seal the splash shield drape around the instrument eyepiece.

In the preferred embodiment, the splash shield of my invention includes a flexible plastic sheet of a size that is sufficient to cover the area of the patient upon which the operation is to be performed. A substantial overlap around the edges of the operating area is desired. The bottom side of the plastic sheet near its top edge carries an adhesive fastener which engages with the patient's body to secure the splash shield in place. A sealable aperture is present in the plastic sheet for accommodating the eyepiece of an optical instrument. The preferred embodiment provides protection from splashing liquid while permitting continued normal use of optical instruments.

In use, the rectangular splash shield of my invention covers the operating area, shielding the physician from splashing blood or irrigation fluid. The physician obtains manual access to the operating area simply by inserting his or her hands underneath the side or bottom edges of the splash shield. The shield can be made of a flexible, transparent plastic, allowing a view of the operating area. As a result, excellent protection without obstruction of the use of optical instruments can be achieved with my invention.

Accordingly, an object of my invention is to provide a splash shield for use in any surgical operation.

An additional object of my invention is to provide a splash shield with the ability to accommodate optical instruments while maintaining a high level of splash protection.

A further object of my invention is to provide a splash shield that may be used to protect a physician during a cystoscopy.

Another object of my invention is to provide a splash shield that is of a shape suitable for accommodation of optical instruments during a cystoscopy.

Other advantages of my invention will become apparent from the drawings, detailed description and claims which follow:

BRIEF DESCRIPTION OF THE DRAWINGS

The novel features of my invention are set forth with particularity in the appended claims. The invention, together with its objects and advantages thereof, may be best understood by reference to the following description taken in conjunction with the accompanying drawings.

DETAILED DESCRIPTION OF THE PREFERRED EMBODIMENT

Figure 1:
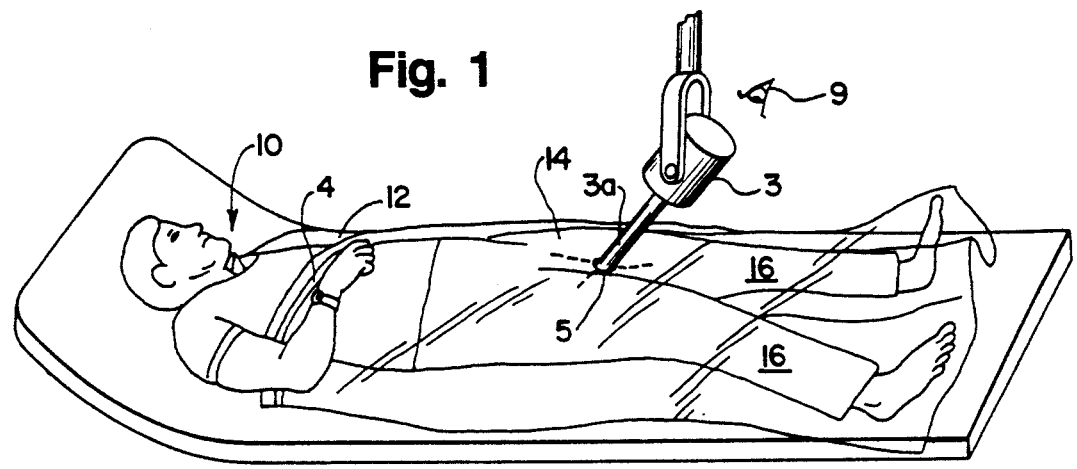
FIG. 1 is a perspective view of my cystoscopy splash shield positioned over a patient.

FIG. 1 shows the cystoscopy splash shield 1 in position over a patient 10. Top portion 2a of plastic sheet 2 is affixed to torso 12 of patient 10 during surgery via hypoallergenic pressure sensitive tape 4. Once affixed to the torso 12 of patient 10, the remaining portion of splash shield 1 is draped over the groin area 14 which is to undergo surgery. Once draped over groin area 14, remaining lower portion 2b of plastic sheet 2 may be further draped between and over patient's legs 16.

Once in place, splash shield 1 is ready to receive and accommodate a medical optical instrument 3 such as a cystoscope or endoscope, or any other suitable surgical instrument such as a catheter. Instrument 3 is inserted through hole 5 in plastic sheet 2. Instrument 3 is secured in place with the assistance of perforations 6 which provide a snap fit over eyepiece 3a of instrument 3. Once eyepiece 3a is satisfactorily positioned within hole 5, adhesive tape 6 is wrapped around the circumference of eyepiece 3a which is surrounded by plastic material immediately around hole 5. The result is an airtight seal around eyepiece 3a.

With instrument 3 in place with top portion 2a of plastic sheet affixed to torso 12 of patient 10 and lower portion 2b draped over and between patient's legs 16, physician 9 is ready to begin surgery on patient 10. The area subject to surgery will be beneath splash shield 1. In the event that fluids (not shown) splash up out of the area under surgery, physician 9 will be protected. The splashed fluids are directed back toward patient 10 to later be absorbed and/or channeled away.

Figure 2:
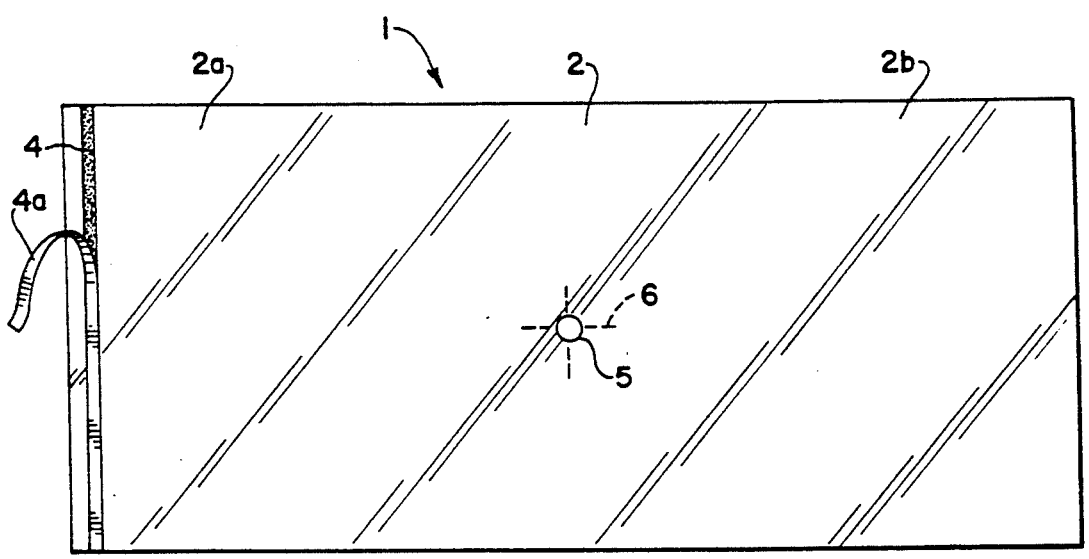
FIG. 2 is a top view of the cystoscopy splash shield.

Turning to FIG. 2, the cystoscopy splash shield 1 is shown laid completely flat. The splash shield 1 includes flexible plastic sheet 2 which forms the overall shape of the splash shield 1. This plastic sheet 2 may be manufactured in various sizes according the requirements of the surgery to be undertaken. The size of plastic sheet 2 may be tailored according to the size of the patient 10 as well. For most operations, it is preferable that plastic sheet 2 be approximately 58 inches long and approximately 26 inches wide. Such a dimension of the overall size of the splash shield 1 can be used in most surgeries.

To adequately repel fluids and resist minor punctures during surgery, it is preferred that the plastic sheet 2 be of at least 1 mil in thickness and that it be manufactured of transparent polyethylene, polypropylene or the like.

The overall shape of plastic sheet 2 is preferably rectangular but may be custom tailored according to the location and type of surgery to be conducted.

Splash shield 1 has an adhesive layer 4 to secure splash shield 1 to patient 10 which preferable extends the entire width of plastic sheet 2. Adhesive layer 4 carries an release layer 4a which is to remain on adhesive layer 4 until splash shield 1 is to be used. When it is time for splash shield 1 to be used for surgery, release layer 4a is removed from adhesive layer 4. Entire splash shield 1 is turned over so the side with adhesive layer 4 is facing patient's torso 12. Splash shield 1 is moved in to the desired position where pressure is then applied to the back of splash shield 1 in the area of adhesive layer 4 to secure splash shield 1 to patient's torso 12. Next, the remaining portion of splash shield 1 is draped over the lower half of patient's body.

Referring to FIG. 2, hole 5 is cut in plastic sheet 2. Perforations 6 are included as tear slits to allow a snap fit over instrument eyepiece 3a. It is desirable that hole 5 be generally circular in shape to accommodate an eyepiece 3a that is substantially circular in cross section. However, hole 5 can be other shapes, such as oval or rectangular, to accommodate eyepieces of varying cross-sectional shapes.

It should be understood that various changes and modifications to the preferred embodiments described herein will be apparent to those skilled in the art. Such changes and modifications can be made to the illustrated embodiments without departing from the spirit and scope of my invention, and without diminishing any attendant advantages of my invention. I intend, therefore, to cover such changes and modifications by the following claims.

I claim:

1. A splash shield for use in surgical operations on a patient that involve the use of instruments, comprising:
    a. a flexible plastic sheet of sufficient size to cover the area of the patient upon which the operation is to be performed, and to provide substantial overlap around the edges of the operating area, said sheet having a top side and a bottom side, and a top edge and a bottom edge;
    b. a sealable aperture in said sheet through which an instrument can be inserted to provide access to the patient while enabling operation of the instrument from said top side of said sheet, wherein said sealable aperture further comprises two lines of perforated tear slits oriented at right angles to each other to form an apex, and a hole located at said apex; and
    c. adhesive fastening means affixed to said bottom side of said sheet, spaced from said top edge and positioned intermediate said top edge and said aperture, and extending across the entire width of said sheet in a direction substantially parallel to said top edge, whereby said sheet can be attached to the patient's body.

2. A splash for use in surgical operations on a patient that involve the use of optical instruments, comprising:
    a. a flexible plastic sheet of sufficient size to cover the area of the patient upon which the operation is to be performed, and to provide substantial overlap around the edges of the operating area, said sheet having a top side and a bottom side, and a top edge and a bottom edge;
    b. a sealable aperture in said sheet through which the eyepiece of an optical instrument can be inserted to provide access to the patient while enabling operation and viewing of the optical instrument from said top side of said sheet, wherein said sealable aperture further comprises two lines of perforated tear slits oriented at right angles to each other to form an apex, and a hole located at said apex; and c. adhesive fastening means affixed to said bottom side of said sheet, spaced from said top edge and positioned intermediate said top edge and said aperture, and extending across the entire width of said sheet in a direction substantially parallel to said top edge, whereby said sheet can be attached to a conventional surgical drape.

* * * * *